United States Patent
Boyle, Jr.

(10) Patent No.: US 10,667,884 B2
(45) Date of Patent: Jun. 2, 2020

(54) BODY-SPACE DRAINAGE-TUBE DEBRIS REMOVAL

(71) Applicant: ClearFlow, Inc., Anaheim, CA (US)

(72) Inventor: Edward M. Boyle, Jr., Bend, OR (US)

(73) Assignee: CLEARFLOW, INC., Irvine, CA (US)

( * ) Notice: Subject to any disclaimer, the term of this patent is extended or adjusted under 35 U.S.C. 154(b) by 205 days.

(21) Appl. No.: 15/421,650

(22) Filed: Feb. 1, 2017

(65) Prior Publication Data

US 2017/0135780 A1    May 18, 2017

Related U.S. Application Data

(63) Continuation of application No. 14/255,720, filed on Apr. 17, 2014, now Pat. No. 9,597,159, which is a
(Continued)

(51) Int. Cl.
*A61B 90/70* (2016.01)
*A61M 27/00* (2006.01)
(Continued)

(52) U.S. Cl.
CPC ........... *A61B 90/70* (2016.02); *A61M 1/0039* (2013.01); *A61M 16/0463* (2013.01);
(Continued)

(58) Field of Classification Search
CPC .............. A61B 90/70; A61B 2090/701; A61B 2217/005; A61M 27/00; A61M 2025/0019; A61M 2210/101
See application file for complete search history.

(56) References Cited

U.S. PATENT DOCUMENTS 958,854 A * 5/1910 Bunn ........................... 27/24.2
3,416,532 A   12/1968 Richard et al.
(Continued)

FOREIGN PATENT DOCUMENTS

DE   S8906380 T2   1/1994
EP   1197177 A2    4/2002
(Continued)

OTHER PUBLICATIONS

Supplementary European Search Report issued in corresponding European Patent Application No. 04 75 1217, dated May 10, 2016, 4 pages.
(Continued)

*Primary Examiner* — Bradley J Osinski
(74) *Attorney, Agent, or Firm* — Pearne & Gordon LLP

(57) ABSTRACT

In accordance with embodiments of the present invention, a debris removal system is provided for a body-space drainage system having one or more body tubes with a body tube lumen disposed therein. The debris-removal system comprises an elongated cleaning member and a cleaning head adapted to be advanced distally at least a portion of a length of the body tube lumen to dislodge debris therein. A collapsible sheath can be used to maintain a sterile field in the body tube lumen while the cleaning member is being used by enclosing at least a portion of the cleaning member that is not contained within the body tube lumen, and permitting external digital manipulation of the cleaning member through the sheath to advance and/or retract the cleaning member, and cleaning head, in the body tube lumen.

11 Claims, 12 Drawing Sheets

Related U.S. Application Data continuation of application No. 12/914,693, filed on Oct. 28, 2010, now Pat. No. 8,702,662, which is a continuation of application No. 10/555,130, filed as application No. PCT/US2004/013728 on May 3, 2004, now Pat. No. 7,854,728.

(60) Provisional application No. 60/467,391, filed on May 2, 2003, provisional application No. 60/555,550, filed on Mar. 22, 2004.

(51) Int. Cl.
*A61M 1/00* (2006.01)
*A61M 16/04* (2006.01)
*A61M 25/00* (2006.01)

(52) U.S. Cl.
CPC .......... *A61M 27/00* (2013.01); *A61M 27/002* (2013.01); *A61B 2090/701* (2016.02); *A61B 2217/005* (2013.01); *A61M 2025/0019* (2013.01); *A61M 2027/004* (2013.01); *A61M 2205/0205* (2013.01); *A61M 2205/0216* (2013.01); *A61M 2210/101* (2013.01)

(56) References Cited

U.S. PATENT DOCUMENTS

| | | |
|---|---|---|
| 3,946,741 A | 3/1976 | Adair |
| 3,957,054 A | 5/1976 | McFarlane |
| 3,991,762 A | 11/1976 | Radford |
| 4,006,743 A | 2/1977 | Kowarski |
| 4,056,104 A | 11/1977 | Jaffe |
| 4,148,319 A | 4/1979 | Kasper et al. |
| 4,228,802 A | 10/1980 | Trott |
| 4,257,422 A | 3/1981 | Duncan |
| 4,317,452 A | 3/1982 | Russo et al. |
| 4,324,262 A | 4/1982 | Hall |
| 4,429,693 A | 2/1984 | Blake et al. |
| 4,445,897 A | 5/1984 | Ekbladh et al. |
| 4,465,481 A | 8/1984 | Blake |
| 4,523,920 A | 6/1985 | Russo |
| 4,569,344 A | 2/1986 | Palmer |
| 4,638,539 A | 1/1987 | Palmer |
| 4,692,153 A | 9/1987 | Berlin et al. |
| 4,696,296 A | 9/1987 | Palmer |
| 4,698,058 A | 10/1987 | Greenfeld et al. |
| 4,706,671 A | 11/1987 | Weinrib |
| 4,723,549 A | 2/1988 | Wholey et al. |
| 4,728,319 A | 3/1988 | Masch |
| 4,762,125 A | 8/1988 | Leiman et al. |
| 4,771,772 A | 9/1988 | DeWitt |
| 4,781,678 A | 11/1988 | de Couet et al. |
| 4,865,030 A | 9/1989 | Polyak |
| 4,865,586 A | 9/1989 | Hedberg |
| 4,889,106 A | 12/1989 | Watanabe |
| 4,909,781 A | 3/1990 | Husted |
| 4,921,488 A | 5/1990 | Maitz et al. |
| 4,950,232 A | 8/1990 | Ruzicka et al. |
| 4,967,743 A | 11/1990 | Lambert |
| 5,003,657 A | 4/1991 | Boiteau et al. |
| 5,009,659 A | 4/1991 | Hamlin et al. |
| 5,062,835 A | 11/1991 | Maltz et al. |
| 5,073,164 A | 12/1991 | Hollister et al. |
| 5,100,395 A | 3/1992 | Rosenberg |
| 5,141,503 A | 8/1992 | Sewell, Jr. |
| 5,168,593 A * | 12/1992 | Poje .................. A46B 3/18 15/104.2 |
| 5,188,618 A * | 2/1993 | Thomas ............. A61M 1/0084 604/267 |
| 5,215,522 A | 6/1993 | Page et al. |
| 5,240,675 A * | 8/1993 | Wilk .................. A61B 1/122 15/104.05 |
| 5,260,020 A | 11/1993 | Wilk et al. |
| 5,261,877 A | 11/1993 | Fine et al. |
| 5,297,310 A | 3/1994 | Cox et al. |
| 5,336,177 A | 8/1994 | Marcus |
| 5,349,950 A | 9/1994 | Ulrich et al. |
| 5,370,610 A | 12/1994 | Reynolds |
| 5,490,503 A | 2/1996 | Hollister |
| 5,505,713 A | 4/1996 | Van Antwerp |
| 5,514,112 A | 5/1996 | Chu et al. |
| 5,520,635 A | 5/1996 | Gelbfish |
| 5,522,801 A | 6/1996 | Wang |
| 5,536,248 A | 7/1996 | Weaver et al. |
| 5,538,511 A | 7/1996 | Van Antwerp |
| 5,599,299 A | 2/1997 | Weaver et al. |
| 5,599,300 A | 2/1997 | Weaver et al. |
| 5,630,823 A | 5/1997 | Schmitz-Rode et al. |
| 5,643,229 A | 7/1997 | Sinaiko |
| 5,653,696 A | 8/1997 | Shiber |
| 5,688,234 A | 11/1997 | Frisbie |
| 5,693,011 A | 12/1997 | Onik |
| 5,715,815 A | 2/1998 | Lorenzen et al. |
| 5,768,741 A | 6/1998 | Leiman et al. |
| 5,772,261 A | 6/1998 | Magram |
| 5,788,678 A | 8/1998 | Van Antwerp |
| 5,788,681 A | 8/1998 | Weaver et al. |
| 5,788,710 A | 8/1998 | Bates et al. |
| 5,807,330 A | 9/1998 | Teitelbaum |
| 5,830,127 A | 11/1998 | DeCastro |
| 5,843,028 A | 12/1998 | Weaver et al. |
| 5,868,720 A | 2/1999 | Van Antwerp |
| 5,895,398 A | 4/1999 | Wensel et al. |
| 5,897,534 A | 4/1999 | Heim et al. |
| 5,902,314 A | 5/1999 | Koch |
| 5,911,710 A | 6/1999 | Barry et al. |
| 5,911,734 A | 6/1999 | Tsugita et al. |
| 5,913,852 A | 6/1999 | Magram |
| 5,921,952 A | 7/1999 | Desmond, III et al. |
| 5,928,218 A | 7/1999 | Gelbfish |
| 5,931,821 A | 8/1999 | Weilbacher et al. |
| 5,957,932 A | 9/1999 | Bates et al. |
| 5,964,223 A | 10/1999 | Baran |
| 5,989,241 A | 11/1999 | Plishka et al. |
| 6,045,623 A | 4/2000 | Cannon |
| 6,080,170 A | 6/2000 | Nash et al. |
| 6,082,361 A * | 7/2000 | Morejon .......... A61M 16/0463 128/207.14 |
| 6,129,697 A | 10/2000 | Drasler et al. |
| 6,168,603 B1 | 1/2001 | Leslie et al. |
| 6,183,450 B1 | 2/2001 | Lois |
| 6,248,100 B1 | 6/2001 | de Toledo et al. |
| 6,264,624 B1 | 7/2001 | Desmond, III et al. |
| 6,299,604 B1 | 10/2001 | Ragheb et al. |
| 6,383,196 B1 | 5/2002 | Leslie et al. |
| 6,436,112 B2 | 8/2002 | Wensel et al. |
| 6,454,775 B1 | 9/2002 | Demarais et al. |
| 6,485,497 B2 | 11/2002 | Wensel et al. |
| 6,508,789 B1 | 1/2003 | Sinnott et al. |
| 6,514,273 B1 | 2/2003 | Voss et al. |
| 6,530,935 B2 | 3/2003 | Wensel et al. |
| 6,547,761 B2 | 4/2003 | Liu |
| 6,562,024 B2 | 5/2003 | Alvarez de Toledo et al. |
| 6,582,400 B1 | 6/2003 | Hawk et al. |
| 6,629,956 B1 | 10/2003 | Polidoro et al. |
| 6,638,253 B2 | 10/2003 | Breznock |
| 6,660,014 B2 | 12/2003 | Demarais et al. |
| 6,663,650 B2 | 12/2003 | Sepetka et al. |
| 6,679,262 B1 | 1/2004 | Morejon |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,699,331 B1 | 3/2004 | Kritzler |
| 6,702,830 B1 | 3/2004 | Demarais et al. |
| 6,730,104 B1 | 5/2004 | Sepetka et al. |
| 6,740,096 B2 | 5/2004 | Teague et al. |
| 6,767,338 B2 | 7/2004 | Hawk et al. |
| 6,780,193 B2 | 8/2004 | Leslie et al. |
| 6,783,536 B2 | 8/2004 | Vilsmeier et al. |
| 6,824,545 B2 | 11/2004 | Sepetka et al. |
| 6,849,061 B2 | 2/2005 | Wagner |
| 6,866,657 B2 | 3/2005 | Shchervinsky |
| 6,893,418 B2 | 5/2005 | Liu |

(56) References Cited

U.S. PATENT DOCUMENTS

| | | | |
|---|---|---|---|
| 6,893,424 | B2 | 5/2005 | Shchervinsky |
| 6,905,484 | B2 | 6/2005 | Buckman et al. |
| 6,945,977 | B2 | 9/2005 | Demarais et al. |
| 7,004,954 | B1 | 2/2006 | Voss et al. |
| 7,101,380 | B2 | 9/2006 | Khachin et al. |
| 7,125,402 | B1 | 10/2006 | Yarger |
| 7,141,038 | B2 | 11/2006 | Whalen et al. |
| 7,229,433 | B2 | 6/2007 | Mullen |
| 7,241,299 | B2 | 7/2007 | Gerard |
| 7,244,251 | B2 | 7/2007 | Shehada et al. |
| 7,252,659 | B2 | 8/2007 | Shehada et al. |
| 7,267,671 | B2 | 9/2007 | Shehada |
| 7,285,126 | B2 | 10/2007 | Sepetka et al. |
| 7,326,197 | B2 | 2/2008 | Breznock et al. |
| 7,338,478 | B2 | 3/2008 | Leiboff |
| 7,338,501 | B2 | 3/2008 | Teague et al. |
| 7,419,483 | B2 | 9/2008 | Shehada |
| 7,610,106 | B2 | 10/2009 | Yacoubian |
| 7,695,467 | B2 | 4/2010 | Breznock et al. |
| 7,780,639 | B2 | 8/2010 | Van Lue |
| 7,799,046 | B2 | 9/2010 | White et al. |
| 7,811,293 | B2 | 10/2010 | Simpson et al. |
| 7,867,241 | B2 | 1/2011 | Brock et al. |
| 7,992,561 | B2 | 8/2011 | Baker, Jr. et al. |
| 8,157,919 | B2 | 4/2012 | Vazales et al. |
| 2001/0018572 | A1 | 8/2001 | Kinsey et al. |
| 2002/0058915 | A1 | 5/2002 | Wakabayashi |
| 2002/0128601 | A1 | 9/2002 | Reilly et al. |
| 2003/0069551 | A1 | 4/2003 | Bradley, III et al. |
| 2003/0216760 | A1 | 11/2003 | Welch et al. |
| 2004/0073243 | A1 | 4/2004 | Sepetka et al. |
| 2004/0092956 | A1 | 5/2004 | Liddicoat et al. |
| 2004/0181191 | A1 | 9/2004 | Teitelbaum |
| 2004/0219028 | A1 | 11/2004 | Demarais et al. |
| 2005/0171478 | A1 | 8/2005 | Selmon et al. |
| 2006/0264974 | A1 | 11/2006 | Khachin et al. |
| 2009/0000045 | A1 | 1/2009 | Kanno et al. |
| 2009/0326513 | A1 | 12/2009 | Deutsch et al. |
| 2011/0023888 | A1 | 2/2011 | Vazales et al. |
| 2011/0098660 | A1 | 4/2011 | Porreca, Jr. |
| 2011/0106019 | A1 | 5/2011 | Bagwell et al. |

FOREIGN PATENT DOCUMENTS

| | | |
|---|---|---|
| WO | 9403226 A1 | 2/1994 |
| WO | 2004108051 A2 | 12/2004 |
| WO | 2005067647 A2 | 7/2005 |
| WO | 2008059647 A1 | 5/2008 |

OTHER PUBLICATIONS

International Search Report and Written Opinion dated Nov. 19, 2004 in related PCT Application No. PCT/US04/13728.
International Search Report dated Oct. 22, 2003 and International Preliminary Examination Report dated Aug. 16, 2004 in PCT Application No. PCT/US01/45648.
Supplementary Partial European Search Report dated Apr. 11, 2006 in European Patent Application No. 01986082.4.
Examination Report issued in corresponding European Patent Application No. 04751217.3 dated Apr. 5, 2019, 7 pages.

* cited by examiner

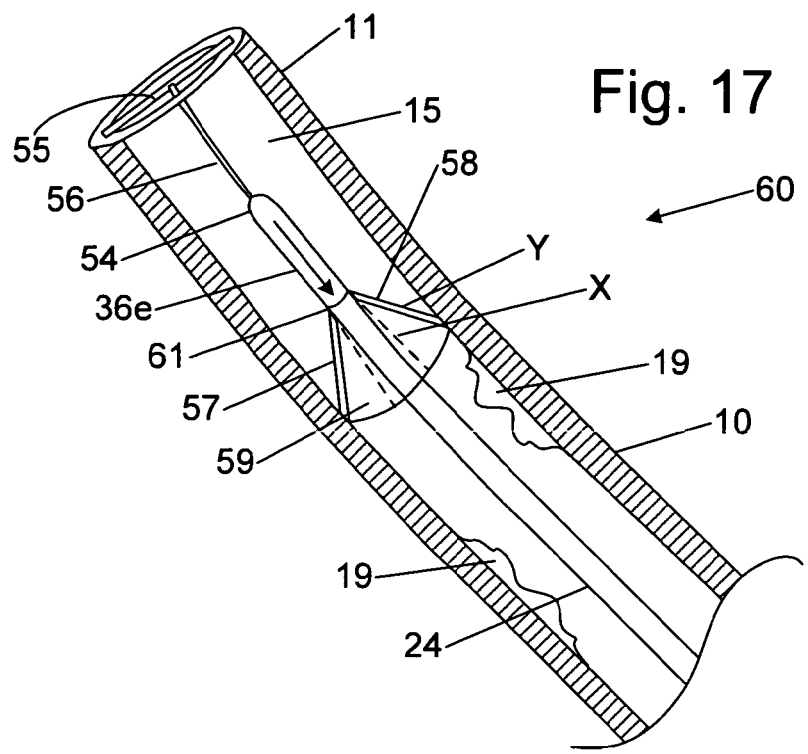
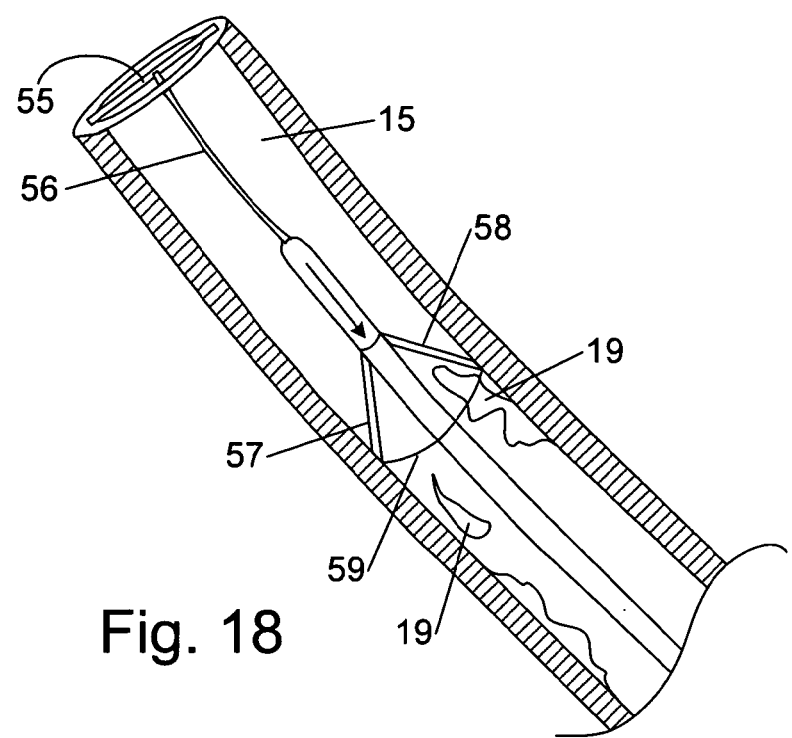

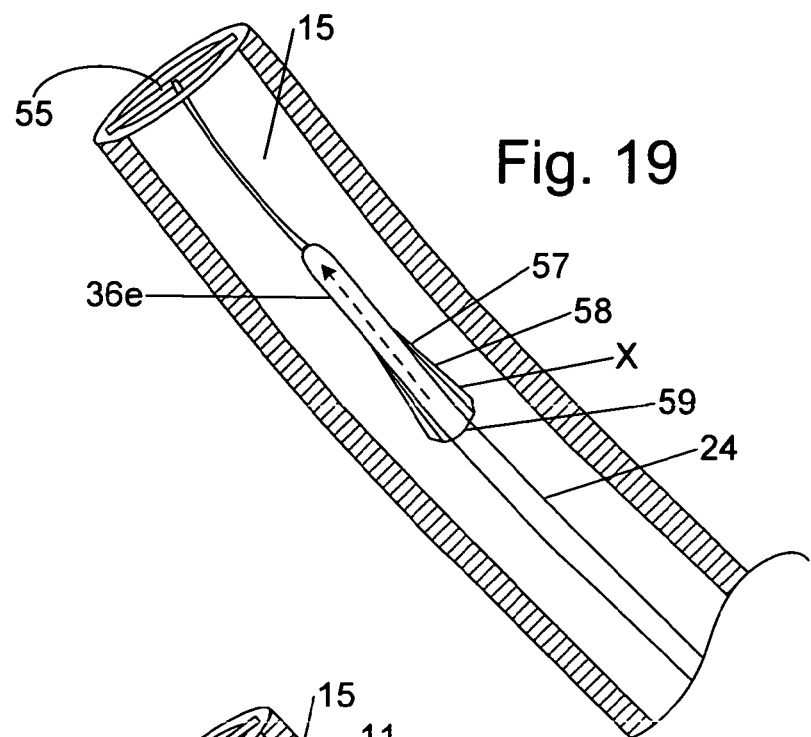
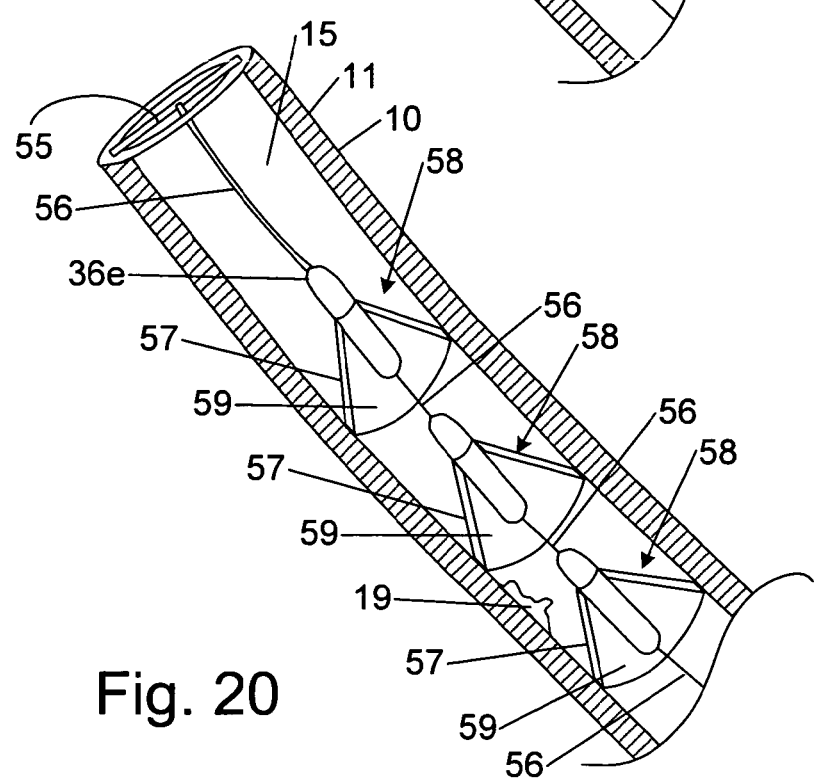

BODY-SPACE DRAINAGE-TUBE DEBRIS REMOVAL

RELATED APPLICATIONS

This application is a continuation of U.S. application Ser. No. 14/255,720 filed Apr. 17, 2014, which is a continuation of U.S. application Ser. No. 12/914,693 filed Oct. 28, 2010, which is a continuation of U.S. application Ser. No. 10/555,130 filed Oct. 31, 2005 (now U.S. Pat. No. 7,854,728, issued Dec. 21, 2010), which application is a National stage entry of PCT Application No. PCT/US04/13728 filed May 3, 2004, which claims priority from U.S. Provisional Application Ser. No. 60/467,391, filed May 2, 2003 and U.S. Provisional Application Ser. No. 60/555,550 filed Mar. 22, 2004, the contents of all of which are hereby incorporated by reference as if recited in full herein for all purposes.

FIELD OF THE INVENTION

The present invention relates to surgical instruments, and more particularly, to body-space drainage systems.

BACKGROUND OF THE INVENTION

Millions of patients have surgical procedures or other conditions that require the placement of a tube or catheter in a body space for drainage of fluids and gases. For example, many chest disorders due to cancer, infection, heart disease, trauma, and other maladies require the temporary placement of a body-space drainage tube (also referred to as a body tube) into one or more spaces within the chest.

Coronary and heart-valve disease patients require temporary pleural and pericardial drainage in the post-operative period. Patients with lung disorders require temporary drainage of the pleural space due to pleural effusion. Patients suffering from chest trauma require various pleural interventions to treat collapsed and injured lungs. Patients with AIDS often have respiratory manifestations, many of which lead to effusions or pneumothoraces that require drainage from the chest.

A chest tube is a type of body-space drainage tube placed in the chest in a process known as tube thoracostomy. The chest tube is part of a drainage system that also comprises a drainage canister used to collect the drained fluids. In some cases, a vacuum is drawn out of the drainage canister to help expedite the drawing of fluids, gases, or both from the chest. While design advances have been made in the drainage canister, very little has changed with the chest tube itself.

FIG. 1 is an illustration of a common body-space drainage-tube system 2. The drainage-tube system 2 comprises one or more body tubes 10, corresponding coupler 12, a canister tube 14, a drainage canister 16, and a vacuum source 18. A body tube 10 is a long, semi-stiff, clear plastic tube having a body-tube distal end 11 that is inserted into the chest or other body space (or body cavity) and a body-tube proximal end 13 that extends outside of the body for coupling with the canister tube 14 via the coupler 12. The body tube 10 provides a fluid path from the body space to the canister tube 14, so as to drain fluid, gas, or both from the body space. In a system known as a closed-suction drainage system, additional components, such as a vacuum source 18 creates low pressure in the canister to draw the fluids, gases, or both out of the body space and into the drainage canister 16.

Body tubes 10 are used to treat may medical conditions. For example, if a lung is compressed due to a collection of fluid, the body-tube distal end 11 of a body tube 10 is inserted into the space between the pleura or within the mediastinum. This placement of a body tube 10 inside the chest drains the collection of fluid and allows the lung to re-expand.

Body tubes 10, especially the larger variety, are inserted mostly by surgeons, but also by pulmonologists, radiologists, critical-care physicians, primary-care doctors, and emergency personnel. Large diameter, large lumen body tubes drain thick pleural fluids more effectively than smaller tubes, in part because a bigger lumen can tolerate more debris without clogging than a smaller lumen. Large-diameter body tubes are not always well tolerated by the patient due to pain, however, and the inability to direct the insertion can lead to incorrect placement. Even the larger tubes can become clogged with blood clots and fibrinous material.

Bleeding often occurs after heart surgery or trauma. When this occurs, the blood can clot in the tube inside the patient, impairing the function of the body tube. Bleeding and clotting in the tube in this circumstance can be life threatening for two reasons. First, clinicians carefully monitor the amount of blood that comes out of the tube as a measure of the seriousness of the amount of bleeding. If blood pools in the chest, for example, then the measurement omits the pooled blood, because it is not draining through the body tube. The patient consequently can lose a large volume of blood without awareness of the health care practitioner and thus, without treatment for the blood loss. This blood loss can have severe hemodynamic consequences, including death. Second, if blood pools in the pericardial space, it can compress the structures of the heart, impairing the return of blood to the heart, and thus the ability of the ventricle to fill and empty. This condition, called pericardial tamponade, likewise can be fatal.

When clinicians caring for patients in the perioperative period following surgery and trauma notice a clot forming in the body tube, they often undertake various measures to try to remove the blood clot. One method is to simply tap the body tube to try to break up the clot. Another method is to "milk the tube," which involves using fingers (or a rudimentary device made from a pair of pliers with added roller heads) to compress the body tube over the clot to break up the clot. This method has the effect of pulling some of the clot towards the canister tube 14 that goes to the drainage canister 16. In another method, called "fan folding," the clinician bends the body tube in various ways in an attempt to break up any long clots and to facilitate flow to the canister. Any manipulation of a body tube in this fashion can be quite painful to the patient.

Another technique is known as "stripping." In this technique, the clinician uses two or more lubricated fingers to compress, or pinch, the body tube near its entry point into the body. The clinician then slides the pinching fingers along the body tube, towards the drainage canister 16. Repeating this motion tends to move clots and debris toward the canister. This technique is only marginally successful. Further, the technique is known to generate short bursts of strong negative pressure at the ends of the body tube. This negative pressure causes a suction effect that can be dangerous because it can yield pressures of up to—300 cm of water adjacent to suture lines on, for example, coronary anastomosis. The resulting forces can damage the work that was done surgically during the operation. This damage is potentially life threatening.

None of these non-invasive techniques for removing debris from the body tube are uniformly successful, and all of them consume valuable time in the postoperative period.

More-drastic methods also exist. These methods are more effective at cleaning—but more risky to the patient. In one scenario, a sterile field is made up, the body tube is disconnected at the coupler 12, and a suction catheter is run up the body tube to clear the debris.

This open-suction technique is generally effective, but it is highly undesirable for several reasons. First, it violates the sterile internal environment of the body-space drainage tube system, potentially introducing bacteria inside the patient's body. Second, for body tubes placed in the chest, it breaks the seal between the body tube and the canister, causing a loss of the physiologic negative pressure inside the chest. As a result, the lungs can collapse (pneumothorax) while body-tube cleaning is being carried out. Finally, it is time-consuming for the nurses or doctors to perform the procedure.

Because of the fear of clogging, clinicians often place more than one body tube, creating auxiliary drainage capacity but worsening pain and potential complications. After the patient makes it through the initial stage of recovery, when clogging can be life threatening, the patient is left with several large-diameter body tubes passing through skin, muscle, and other tissues to reach the body space to be drained or treated.

Chest tubes, for example, typically pass through the ribs of the chest wall, where the tubes lie next to the lung and along the pleura. This placement means that any movement, such as cough, is quite painful. Body tubes are also notorious sites for infection, and multiple tubes increase this risk. When the tubes are left in place for more than a day or so, clogging becomes an issue, as fibrin and other material form in the end of the tube, impairing its function. In support of these concepts, body tubes almost always have a significant clot in the distal end when removed. Any body tube left in place for several days will eventually fail (called a "dead tube") due to clogging. To avoid the danger and hassle of dealing with clogged tubes, surgeons choose large-lumen body tubes and place multiple body tubes, especially after heart surgery, lung surgery, or trauma.

Solving the issue of clogging will allow body tubes to function with better safety and less nursing care. Devices and methods are needed in the art that effectively eliminates clogging and clotting in body tubes, reducing the need for painful and ineffective manipulations of the tubes, and thus reducing the trauma around the tube that can contribute to bleeding, tissue injury, and infection. A benefit will be that smaller body tubes, and perhaps fewer body tubes, can be used, since the reason to use the larger-diameter tubes is to facilitate evacuation of debris and clots that tend to more easily obstruct the smaller tubes. The net result will be reduced pain, faster recovery, and less cost.

Because larger body tubes require more specialty expertise to place, they are usually placed only by surgeons, with pulmonologists or others placing smaller, less effective body tubes. The availability of effective body tubes at smaller diameters will increase the number of clinicians who can insert and manage those tubes.

SUMMARY OF THE INVENTION

Embodiments of the present invention increase the efficiency of body-space drainage-tube systems by incorporating a debris-removal system to keep the body tube clear of clots and other debris. Embodiments of the present invention provide a body-tube cleaning and clearing apparatus that can be efficiently, easily, and routinely used to maintain the flow within the body tube free from the accumulation of blood, pus, foam, secretions, and other debris. In embodiments in accordance with the present invention, the apparatus are used for removing debris from body tubes such as, but not limited to, chest tubes and catheters. The embodiments eliminate the questionable practices of milking, fan folding, stripping, and open suction, easing patient pain and reducing the risk of infection.

Various embodiments of the present invention provide a sterile sheath around a suction/aspiration catheter with a balloon at the tip that can be slid in and out of a body tube to clear it of clot, fluid, and debris. In one embodiment of the present invention, the body-tube cleaning-apparatus includes an elongate tubular catheter having a diameter smaller than the interior diameter of the body tube. Further, the elongate tubular catheter includes a distal end that is structured to be introduced and extended into the lumen of the body tube. The tip of the catheter is blunt and rounded to avoid direct injury to the internal thoracic organs if it should exit the body-tube distal end. The sides at the body tube distal end have holes for suction. Defined within the elongate tubular member, and extending from generally a proximal end to a distal end is a lumen. The lumen provides a fluid path that terminates in an outlet port defined in the elongate tubular catheter. The elongate tubular catheter is encased in a sterile envelope that allows it to be slid in and out of the chest tube without exposing it to the outside, un-sterile, environment.

In accordance with the present invention, a debris-removal system is provided for a body-space drainage system having one or more body tubes, each body tube having a body-tube distal end and a body-tube proximal end with a body tube lumen disposed therein The debris-removal system comprises a cleaning member, a collapsible sheath, and a coupler. Wherein the cleaning member is an elongated member having a cleaning member distal end and a cleaning member proximal end, the cleaning member distal end adapted to enter the body tube lumen at or near the body-tube proximal end and adapted to be advanced distally at least a portion of a length of the body tube lumen. The collapsible sheath is adapted to contain at least a portion of the cleaning member that is not contained within the body tube lumen. The collapsible sheath is flexible so as to allow external digital manipulation of the cleaning member proximal end within of the collapsible sheath.

In accordance with another embodiment, the debris-removal system provides wherein the collapsible sheath is adapted for permitting advancement, retraction and manipulation of the cleaning member within the body tube lumen from outside of the collapsible sheath. In accordance with another embodiment, the debris-removal system provides wherein the collapsible sheath is adapted to contain a fully retracted cleaning member. In accordance with another embodiment, the debris-removal system provides wherein the collapsible sheath adapted to couple at or near the proximal end of the body tube in fluid tight and sterile seal engagement with the body tube lumen.

In accordance with another embodiment, the debris-removal system provides wherein the cleaning member is adapted to be advanced and retracted within the body tube lumen without breaking the sterile seal engagement.

In accordance with another embodiment, the debris-removal system provides wherein the coupler comprises a body tube port adapted to couple with the body tube, a canister tube port adapted to couple with the canister tube, and a collapsible sheath port adapted to couple the collapsible sheath, wherein the coupler-defines a passage in communication with the body tube port, the canister tube port and the collapsible sheath port, the passage adapted to receive the cleaning member. In accordance with another embodiment, the debris-removal system provides wherein the coupler is adapted to provide a removable coupling between the debris-removal system and the drainage system. In accordance with another embodiment, the debris-removal system provides wherein the cleaning member is a flexible filament. In accordance with another embodiment, the debris-removal system provides wherein the flexible filament is selected from a list consisting of semi-rigid wire, plastic rod, and tubing. In accordance with another embodiment, the debris-removal system provides wherein the flexible filament is adapted to mechanically clean the body tube lumen using mechanical dislodgment of the debris, the flexible filament being sufficiently flexible to traverse the curvature of the body tube lumen and sufficiently rigid so as to advance through the body tube lumen by manipulation from about the cleaning member proximal end and to dislodge and/or break up foreign matter within the body tube lumen as it makes contact with the foreign matter.

In accordance with another embodiment, the debris-removal system provides wherein the cleaning member distal end comprises a cleaning member distal tip adapted to provide a rough abrasive surface so as to assist in dislodging foreign matter within the body tube lumen. In accordance with another embodiment, the debris-removal system provides wherein the debris-removal system further comprises a filament manipulation device removably coupled with the cleaning member proximal end and adapted to impart vibratory excitation thereto.

In accordance with another embodiment, the debris-removal system provides wherein the collapsible sheath comprises a collapsible sheath proximal end adapted to couple with the cleaning member proximal end, the debris-removal system further comprising a filament manipulation device removably coupled with the collapsible sheath proximal end. In accordance with another embodiment, the debris-removal system provides wherein the filament manipulation device comprises an ultrasonic transducer that couples sonic energy to the cleaning member. In accordance with another embodiment, the debris-removal system provides wherein the debris-removal system further comprises a filament manipulation device removably coupled with the cleaning member proximal end, the filament manipulation device adapted to couple with the collapsible sheath proximal end and impart a circulatory motion to the cleaning member.

In accordance with another embodiment, the debris-removal system provides wherein the collapsible sheath proximal end comprises a rotatable coupling adapted to couple the cleaning member with the manipulation device, the rotatable coupling adapted to provide a fluid and sterile seal while allowing the manipulation member to rotate the cleaning member.

In accordance with another embodiment, the debris-removal system provides wherein the debris-removal system further comprises a tubular filament comprising an elongated tubular filament having a tubular filament proximal end, tubular filament distal end, and a filament lumen therethrough. The filament lumen defining a flow path to and/or from the tubular filament distal end, the tubular filament being sufficiently flexible to traverse curvature of the body tube lumen, but is sufficiently rigid so as to advance through the body tube lumen by pushing from the proximal end and to dislodge and/or break up foreign matter within the body tube lumen.

In accordance with another embodiment, the debris-removal system provides wherein the filament lumen is adapted to provide a suction or vacuum path for the collection and removal of the dislodged debris, the tubular filament distal end adapted for coupling with a vacuum source and adapted to extract foreign material.

In accordance with another embodiment, the debris-removal system provides wherein the debris-removal system is adapted to be coupled to a chest tube in a closed-suction tube system to drain blood and fluid and air from the chest.

In accordance with another embodiment, the debris-removal system provides wherein the tubular filament distal end comprises an angular tip.

In accordance with another embodiment, the debris-removal system provides wherein the debris-removal system further comprises a fluid source, the filament lumen adapted for expelling fluid from the tubular filament distal end.

In accordance with another embodiment, the debris-removal system provides wherein the fluid source is adapted to supply fluid expelled at the tubular filament distal end at a predetermined pressure to mechanically dislodge and/or break up the foreign material.

In accordance with another embodiment, the debris-removal system provides wherein the fluid source is adapted to supply fluid with sonic energy.

In accordance with another embodiment, the debris-removal system provides wherein the fluid source is adapted to provide fluid comprising a solution adapted to assist in the dislodgment, dissolution and/or breakup of the foreign matter.

In accordance with another embodiment, the debris-removal system provides wherein the fluid is a therapeutic agent selected from a list comprising antibiotic agents and anti-neoplastic agents.

In accordance with another embodiment, the debris-removal system provides wherein the cleaning member is a tubular filament comprising a tubular filament distal end having an expandable portion coupled to a filament lumen, the expandable portion adapted to have a relaxed state in which the distal end has a minimal profile and an expanded state wherein the distal end has an enlarged profile, the expandable debris-removal system further comprises an inflatable fluid delivery system adapted to communicate inflation fluid to the expandable portion, the expandable portion adapted to expand by the advancement of inflation fluid from an fluid delivery system, through the lumen to the expandable portion, the inflation fluid controlled at the tubular member proximal end. The expandable portion of the distal tip is adapted to expand under fluid pressure and recoil back to substantially the original position upon withdrawal of the fluid pressure.

In accordance with another embodiment, the debris-removal system provides wherein the expanded portion is adapted to fully occlude the body tube lumen when in the expanded state.

In accordance with another embodiment, the debris-removal system provides wherein the inflatable fluid delivery system comprises a reservoir adapted to be coupled to the lumen at the proximal end of the cleaning member.

In accordance with another embodiment, the debris-removal system provides, wherein the reservoir comprises an elastic bulb, balloon or fluid-filled syringe coupled to the cleaning member through a coupling.

In accordance with another embodiment, the debris-removal system provides wherein the fluid reservoir is provided within the collapsible sheath.

In accordance with another embodiment, the debris-removal system provides wherein the expandable portion comprises an arrowhead or umbrella-shaped profile.

In accordance with another embodiment, the debris-removal system provides wherein the expandable portion is along a portion of the length of the distal end, in fluid communication with the tubular filament lumen and adapted to expand upon presented with fluid pressure, to a larger diameter than a relaxed state.

In accordance with another embodiment, the debris-removal system provides wherein the expandable portion is a plurality of expandable portion spaced a predetermined distance apart along the length of the cleaning member.

In accordance with another embodiment, the debris-removal system provides wherein the distal end further comprises an elastic cord adapted to couple with the body tube distal end so as to provide a restoring force to reposition the cleaning member adjacent the body tube distal end.

In accordance with another embodiment, the debris-removal system provides the distal end further comprising a cross-bar support adapted to couple the cleaning member to the body tube distal end.

In accordance with another embodiment, the debris-removal system provides wherein the expandable portion comprises an umbrella-like expandable portion comprising of a plurality of struts and web, the umbrella-like expandable portion adapted to collapse to a narrow profile, and expand to substantially occlude the body tube lumen.

In accordance with another embodiment, the debris-removal system provides wherein distal end further comprises an elastic cord adapted to couple with the body tube distal end so as to provide a restoring force to reposition the cleaning member adjacent the body tube distal end.

In accordance with another embodiment, the debris-removal system provides wherein the expandable portion comprises a plurality of umbrella-like expandable portions comprising of a plurality of struts and webs, at least two of the plurality of expandable portions coupled to adjacent expandable portions with an elastic cord.

Various embodiments of the present invention, singularly or in combination, are to provide a body-space drainage-tube cleaning apparatus.

DRAWINGS

FIG. 17 is a side view of a distal end of an umbrella cleaning member comprising an umbrella-like expandable portion in accordance with an embodiment of the present invention;

FIG. 18 is a side view of a distal end of a cleaning member of FIG. 17;

FIG. 19 is a side view of a distal end of a cleaning member of FIG. 17;

FIG. 20 is a side view of a distal end of a cleaning member comprising a plurality of umbrella-like expandable portions, in accordance with an embodiment of the present invention.

DESCRIPTION

Figure 1:
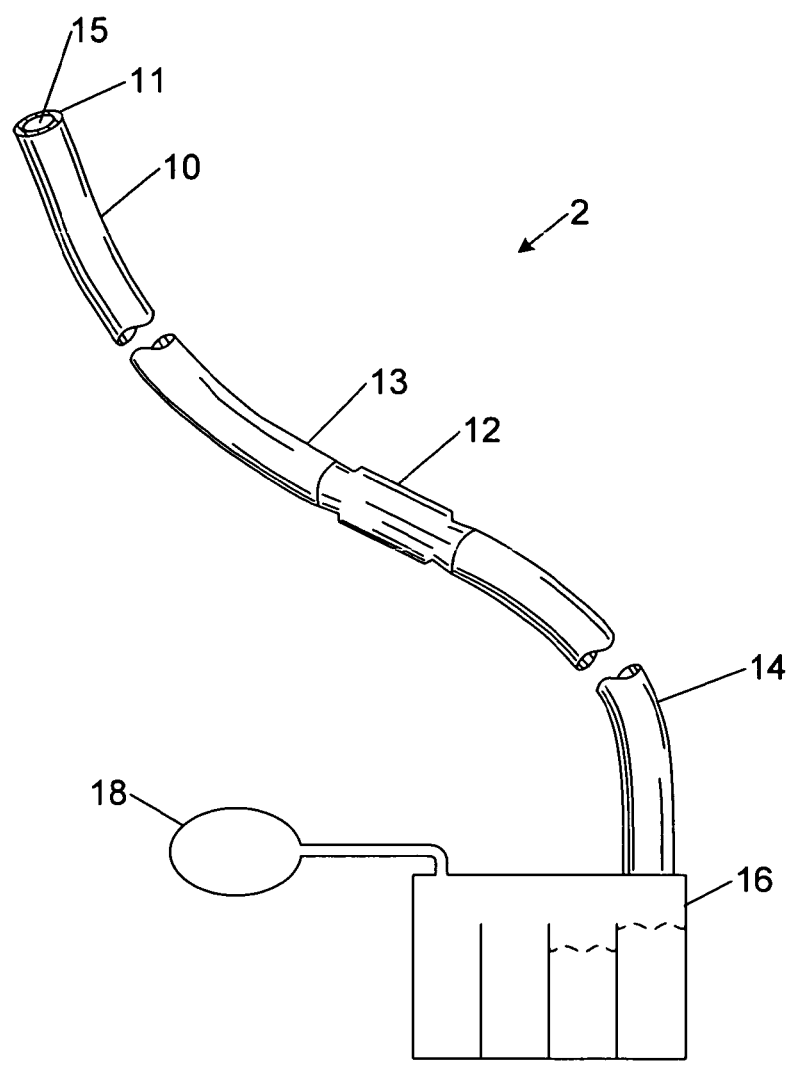
FIG. 1 is a side view of a common body-space drainage-tube system.

Referring again to FIG. 1, a common body-space drainage system 2 comprises one or more body tubes 10, corresponding coupler 12, a canister tube 14, a drainage canister 16, and a vacuum source 18. A body tube 10 is a long, semi-stiff, clear plastic tube having a body-tube distal end 11 and a body-tube proximal end 13 with a body tube lumen 15 disposed therein The body-tube distal end 11 is adapted to be inserted into the chest or other body space (or body cavity) and the body-tube proximal end 13 is adapted to extend outside of the body for coupling with the canister tube 14. Various embodiments in accordance with the present invention are used to clear the body tube lumen 15 of foreign material, such as, but not limited to, blood clot, that can impair the function of the body tube 10. Various embodiments of the present invention are also used to irrigate the body tube 10.

Figure 2:
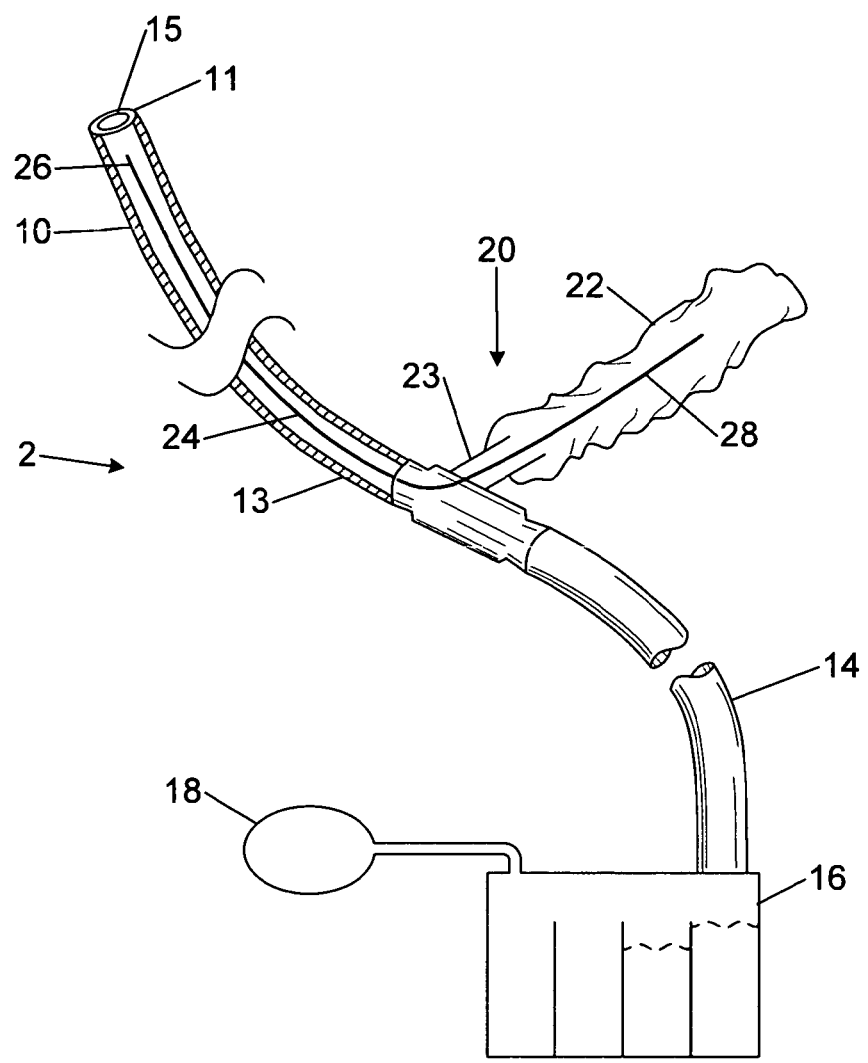
FIG. 2 is a front view of a debris-removal system coupled with a body-space drainage-tube system in accordance with an embodiment of the present invention.

FIG. 2 is a perspective view of a debris-removal system 20 in accordance with an embodiment of the present invention. The debris-removal system 20 comprises a cleaning member 24, a collapsible sheath 22, and a coupler 23. The debris-removal system 20 is shown as assembled onto a body-space drainage system 2.

The cleaning member 24 is an elongated member comprises a cleaning member distal end 26 and a cleaning member proximal end 28. The cleaning member distal end 26 is adapted to enter the body tube lumen 15 at or near the body-tube proximal end 13 and be advanced distally at least a portion of the length of the body tube lumen 15. The collapsible sheath 22 is adapted to contain at least a portion of the cleaning member 24 that is not contained within the body tube lumen 15. The collapsible sheath 22 is adapted to be flexible so as to allow external digital manipulation of the cleaning member proximal end 28 within of the collapsible sheath 22. For example, the collapsible sheath 22 allows for grasping a portion of the cleaning member 24 within the collapsible sheath 22 for advancing, retracting and manipulating the cleaning member 24 within the body tube lumen 15.

The collapsible sheath 22 comprises a suitable material for the particular purpose. In embodiments in accordance with the present invention, the collapsible sheath 22 comprises a flexible film comprising synthetic resinous material, such as, but not limited to, medical grade polyethylene film. The collapsible sheath 22 is manually collapsed, such as between the thumb and index finger of the practitioner, and the like, in order to manipulate the cleaning member 24 contained therein. The collapsible sheath 22 is adapted to retain and maintain a sterile environment, and, were applicable, the vacuum, of the body-space drainage system 2.

In embodiments in accordance with the present invention, the collapsible sheath 22 is adapted to contain a fully retracted cleaning member 24 so as to provide an unobstructed flow path through the body tube lumen 15 to the canister tube 14.

The collapsible sheath 22 is adapted to couple at or near the proximal end 13 of the body tube 10 so as to provide a fluid tight and sterile seal with the body tube lumen 15. The cleaning member 24 can therefore be advanced and retracted within the body tube lumen 15 without the need to break the sterile seal or to interrupt the vacuum of a closed vacuum system.

Figure 3:
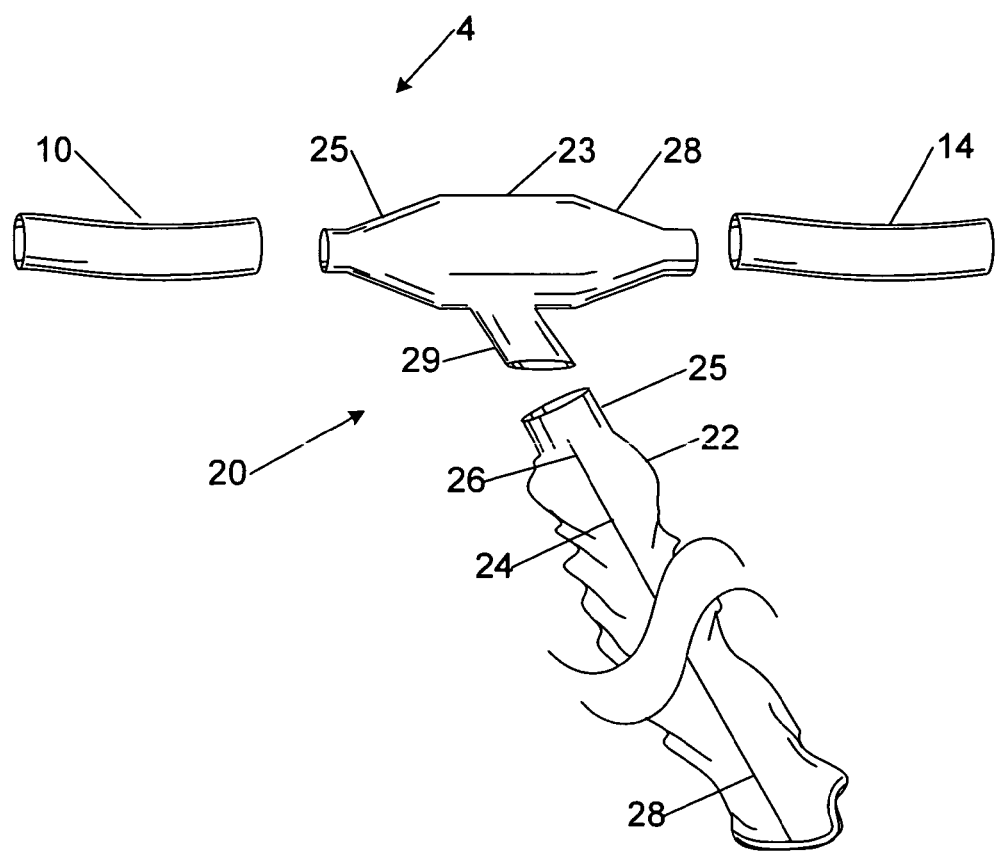
FIG. 3 is an exploded view of a debris-removal system in accordance with an embodiment of the present invention.

FIG. 3 is an exploded view of the debris-removal system 20, in accordance with an embodiment of the present invention. The coupler 23 comprises a body tube port 25, a canister tube port 28, and the collapsible sheath port 29. The body tube port 25 and the canister tube port 28 are adapted to couple with the body tube 10 and canister tube 14, respectively. The collapsible sheath port 29 is adapted to couple the collapsible sheath 22. The coupler 23 is adapted to provide a fluid path between the body tube 10 and the canister tube 14, and a path to insert the cleaning member 24.

In an embodiment in accordance with the present invention, the coupler 23 is adapted to provide a removable coupling between the collapsible sheath 22 and the drainage system 2. The collapsible sheath 22 is coupled to the coupler 23 at the coupling end 25 of the collapsible sheath 22. The collapsible sheath 22 permits the operator to manipulate the cleaning member 24 and insert the cleaning member distal end 26 into the body tube 10 via the collapsible sheath port 29 of the coupler 23 while maintaining sterility and vacuum. The proximal end 28 of the cleaning member 24 remains outside the coupler 23 so that the operator can manipulate the cleaning member 24 with isolation maintained by the collapsible sheath 22.

Embodiments of the present invention provide a coupler 23 to provide use of the debris-removal system 20 without disconnection of the canister tube 14. It is understood that other embodiments are anticipated providing the debris-removal system 20 to couple with a straight coupler 12, as shown in FIG. 1, but requiring the disconnection of the canister tube 14.

Various embodiments of the cleaning member 24 are anticipated, some of which are presented below.

Figure 4:
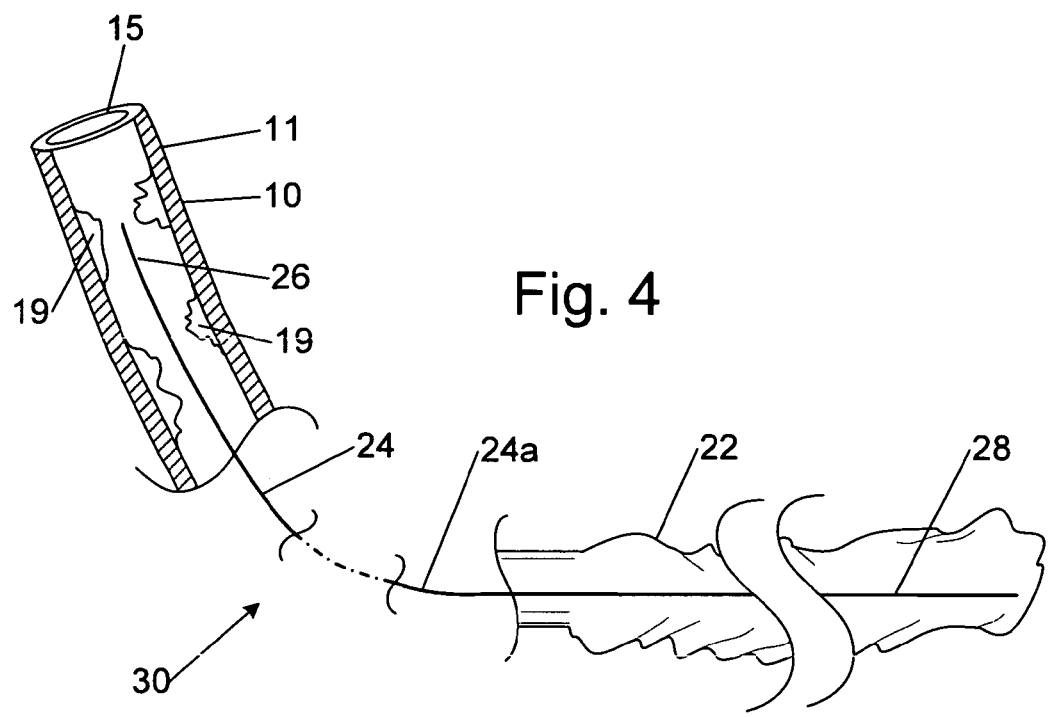
FIGS. 4 and 5 are partial side views of a flexible filament debris-removal system in accordance with an embodiment of the present invention.
Figure 5:
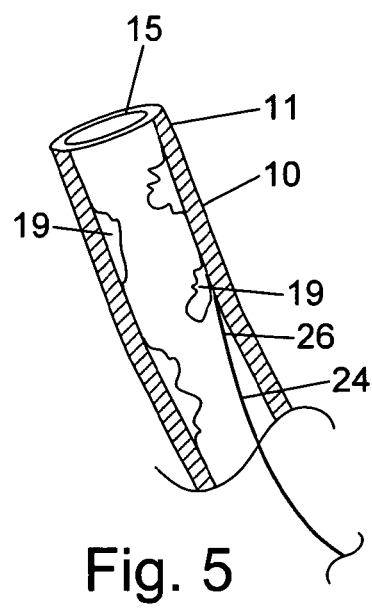

FIGS. 4 and 5 are partial side views of a flexible filament debris-removal system 30, wherein the cleaning member 24 is a flexible filament 24a, in accordance with an embodiment of the present invention. The flexible filament 24a is fabricated from material suitable for the particular purpose, including, but not limited to, polymers, such as, but not limited to polyvinyl chloride, in the form of such as, but not limited to, wire, plastic rod, and tubular members.

The flexible filament is adapted to mechanically clean the body tube lumen 15 using mechanical dislodgment of the foreign material 19. The flexible filament 24a is sufficiently flexible to traverse the curvature of the body tube lumen 15, but is sufficiently rigid so as to prevent buckling when advanced through the body tube lumen 15 by pushing from about the cleaning member proximal end 28 and to dislodge and/or break up foreign material 19 within the body tube lumen 15 as it makes contact with the foreign matter. The foreign material 19 is dislodged from the body tube lumen 15 and carried to the canister (not shown) via the vacuum system (not shown).

Figure 6A:
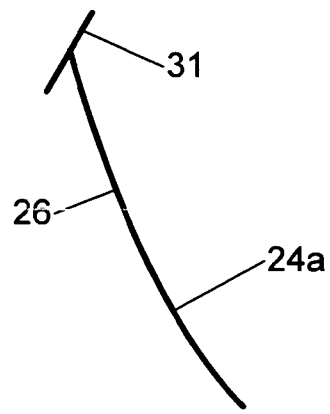
FIG. 6A is a side view of a cleaning member distal end comprising a cleaning head in accordance with an embodiment of the present invention.

FIG. 6A is a side view of a cleaning member distal end 26 comprising a cleaning head 31 that is at an oblique angle relative to the cleaning member, in accordance with an embodiment of the present invention. The cleaning head 31 is adapted to provide additional surface area and/or means for dislodging and/or break up of foreign material 19 within the body tube lumen 15.

Figure 6B:
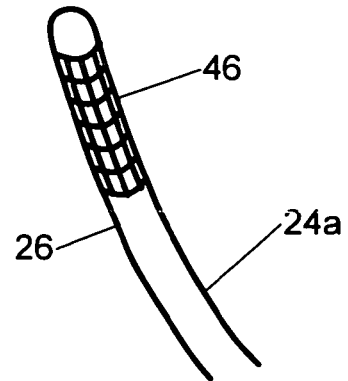
FIG. 6B is a side view of a cleaning member distal end comprising cleaning member distal tip in accordance with embodiments of the present invention.

FIG. 6B is a side view of a cleaning member 24a in accordance with an embodiment of the invention. The cleaning member 24a comprises a cleaning member distal end 26 comprising a cleaning member distal tip 46 adapted to provide an enhanced surface, such as, but not limited to, an abrasive or sharp surface, so as to assist in dislodging foreign material 19 within the body tube lumen 15.

Figure 7:
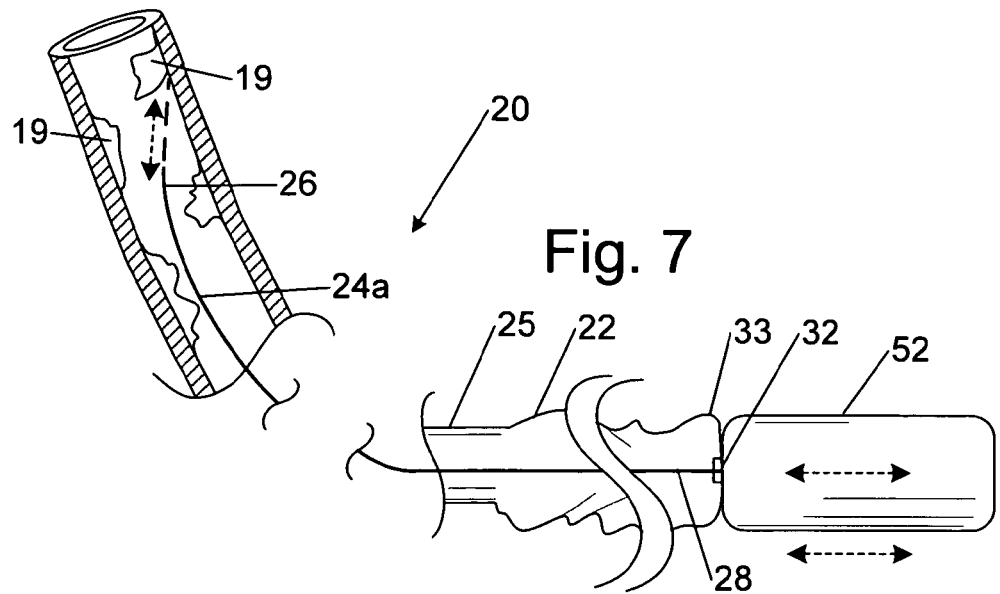
FIG. 7 is a side view of a debris-removal system further comprising a filament manipulation device in accordance with embodiments of the present invention.

FIG. 7 is a side view of a debris-removal system 20 further comprising a filament manipulation device 52, the coupler not shown, in accordance with an embodiment of the present invention. The filament manipulation device 52 is adapted to couple with the cleaning member proximal end 28 and impart vibratory excitation thereto.

The collapsible sheath 22 comprises a collapsible sheath proximal end 33 that is coupled with the cleaning member proximal end 28. The filament manipulation device 52 is adapted to couple with the collapsible sheath proximal end 33 and therefore couple with the cleaning member proximal end 28. In one embodiment, the filament manipulation device 52 imparts a vibratory motion to the cleaning member 24 which provides relative motion to the cleaning member distal tip 26. This relative motion of the cleaning member distal tip 26 assists in the dislodgment and/or breakup of the foreign material 19 when placed in contact therewith.

In another embodiment in accordance with the present invention, the filament manipulation device 53 comprises an ultrasonic transducer that couples sonic energy to, and therefore vibratory motion, the cleaning member 24. A vibratory motion is adapted to induce sonic motion to the cleaning member distal tip 26 as well as any surrounding fluid, further assisting in the breakup and/or dislodgment of the foreign material 19.

Figure 8:
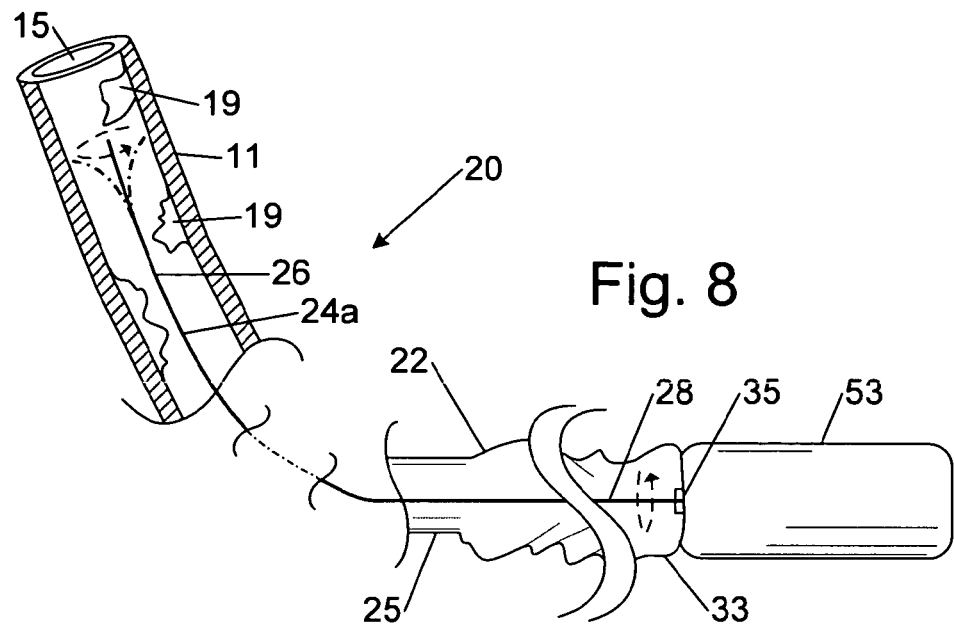
FIG. 8 is a side view of a debris-removal system further comprising another embodiment of a filament manipulation device in accordance with embodiments of the present invention.

FIG. 8 is a side view of a debris-removal system 20 further comprising another embodiment of a filament manipulation device 53, in accordance with the present invention. The collapsible sheath 22 comprises a collapsible sheath proximal end 33 that is coupled with the cleaning member proximal end 28. The filament manipulation device 53 is adapted to couple with the collapsible sheath proximal end 33 and therefore couple with the cleaning member proximal end 28. In an embodiment, the filament manipulation device 53 imparts a rotary motion to the cleaning member which provides rotary motion, or whipping motion, to the cleaning member distal tip 26. This rotary motion of the cleaning member distal tip 26 assists in the dislodgment and/or breakup of the foreign material 19.

In an embodiment in accordance with the present invention, the collapsible sheath proximal end 33 comprises a rotatable coupling 35. The rotatable coupling 35 is adapted to couple the cleaning member proximal end 33 with the manipulation device 53. The rotatable coupling 35 is adapted to provide a fluid and sterile seal while allowing the manipulation device 53 to rotate the cleaning member 24a.

It is anticipated that the manipulation device 53 can be adapted to provide various motions to the cleaning member 24a to assist in the breakup and/or removal of the foreign material 19. These motions include, but are not limited to, vibration, rotation, oscillatory rotation, and combinations there of.

Figure 9:
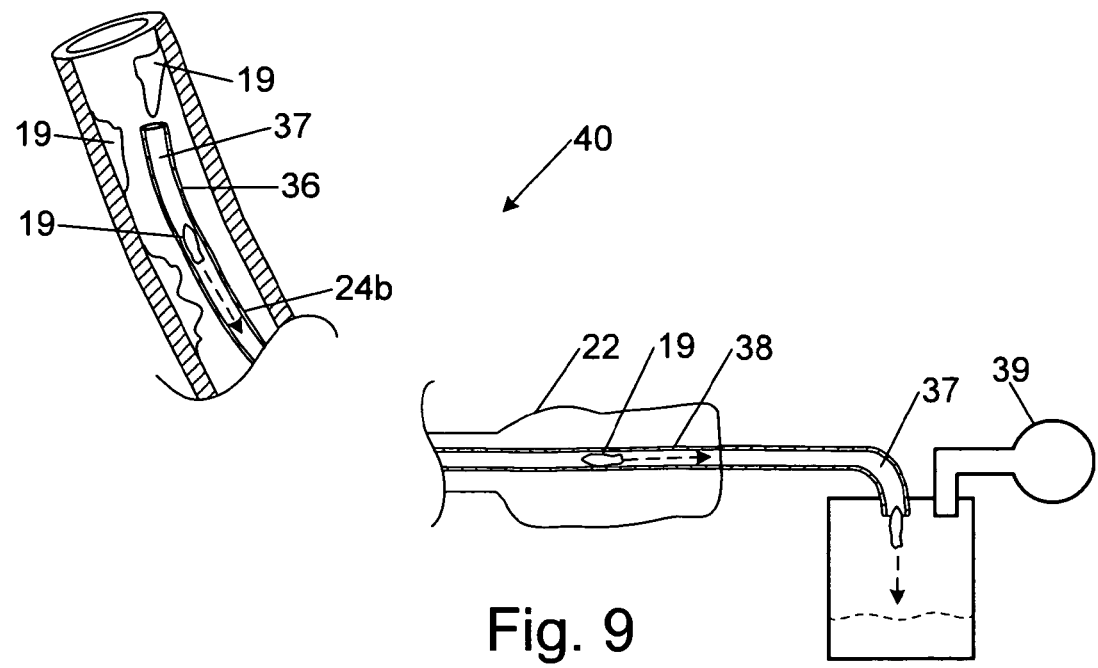
FIG. 9 is a partial side view of a tubular filament debris-removal system, wherein the cleaning member is a tubular filament, in accordance with embodiments of the present invention.

FIG. 9 is a partial side view of a tubular filament debris-removal system 40, coupler not shown, wherein the cleaning member 24 is a tubular filament 24b, in accordance with an embodiment of the present invention. The tubular filament 24b comprises a tubular filament proximal end 38, tubular filament distal end 36, and a filament lumen 37 there through. As with the filament member 24a described above, the tubular filament 24b is adapted to mechanically clean the body tube lumen 15 by mechanical breakup and/or dislodgment of the foreign material 19.

In another embodiment in accordance with the present invention, the filament lumen 37 provides a flow path to and/or from the tubular filament distal end 36 and the tubular filament proximal end 38. The tubular filament 24b is sufficiently flexible to traverse curvature of the body tube lumen 15, but is sufficiently rigid so as to advance through the body tube lumen 15 without buckling by pushing from the tubular filament proximal end 38 and to dislodge and/or break up foreign material 19 within the body tube lumen 15.

In one embodiment as shown in FIG. 9, the filament lumen 37 is adapted to provide a suction or vacuum path for the collection and removal of the dislodged foreign material 19. The tubular filament proximal end 38 is coupled with a vacuum source 39 adapted to extract the foreign material 19. By way of example, wherein the debris-removal system 40 is coupled to a chest tube in a closed-suction tube system to drain blood and fluid and air from the chest, this embodiment of the present invention provides a second closed-suction tube system to clear the body tube lumen 15, in essence, providing a double closed-suction system.

A tubular filament 24b suitable for the particular purpose includes, but is not limited to, a suction catheter adapted to vacuum-remove loosened foreign material 19. In accordance with an embodiment of the present invention, a debris-removal system comprises a closed tracheal suction system used for the drainage of endotracheal tubes and a coupler 23, suitable to provide access to the closed tracheal suction system and the endotracheal tubes.

Figure 10:
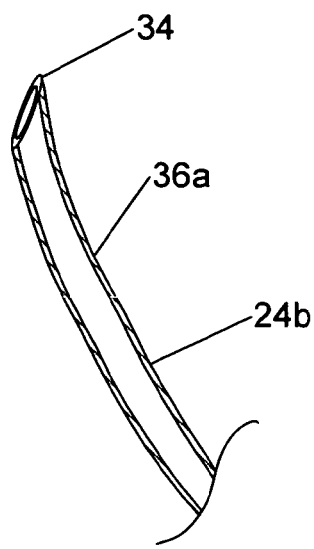
FIG. 10 is a partial side view of a tubular filament distal end comprising an angular tip, in accordance with an embodiment of the present invention.

FIG. 10 is a partial side view of a tubular filament 24b including a tubular filament distal end 36a comprising an obliquely angular tip 34, in accordance with an embodiment of the present invention. The angular tip 34 provides an aggressive structure to assist in the dislodgment of the foreign material.

It is anticipated that the tubular filament embodiments can be augmented with embodiments of the manipulation device 52 as presented previously.

Figure 11:
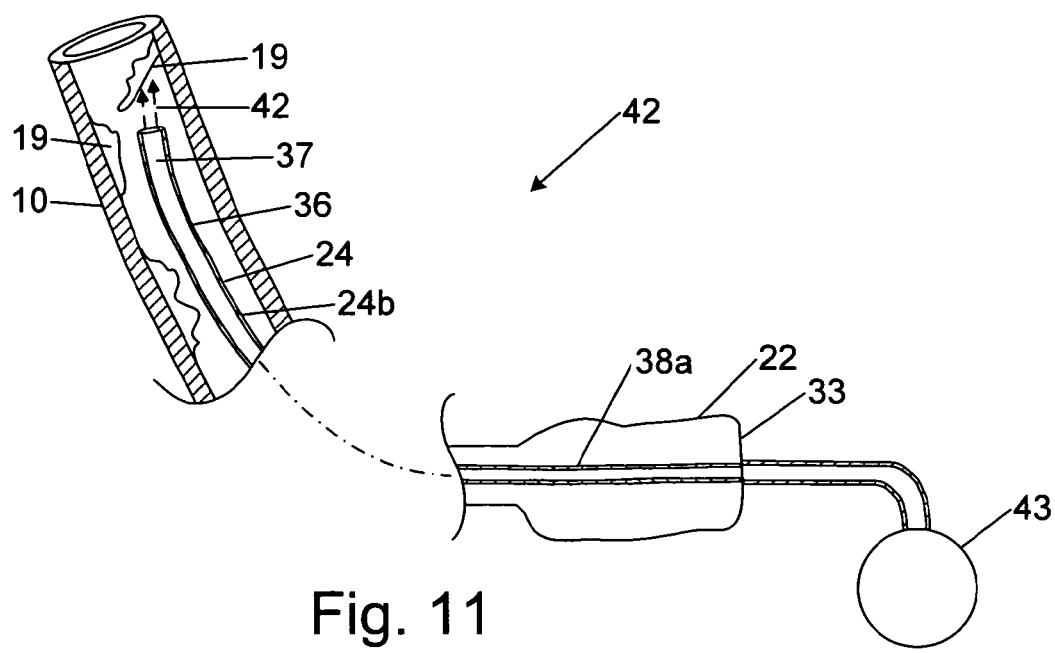
FIG. 11 is a partial side view of a tubular filament debris-removal system adapted for expelling fluid from the tubular filament distal end, in accordance with an embodiment of the present invention.

FIG. 11 is a partial side view of the tubular filament debris-removal system 42, wherein the cleaning member 24 is a tubular filament 24b with a filament lumen 37 adapted for expelling fluid from the tubular filament distal end 36, in accordance with the present invention. A tubular filament 24b suitable for the particular purpose includes, but is not limited to, a catheter with a distal irrigation port adapted to expel fluid.

In one embodiment in accordance with the present invention, the fluid is expelled from the tubular filament distal end 36 at a predetermined pressure so as to assist in the dislodgment and/or break up of the foreign material 19. A fluid jet 42 is produced so as to provide an aggressive cleaning action. The fluid jet 42 is adapted to mechanically dislodge and/or break up the foreign material. The fluid jet 42 can be continuous or pulsed.

In another embodiment in accordance with the present invention, the fluid jet 42 is provided with sonic energy to provide vibratory action to the fluid to further assist in the cleaning action.

In an embodiment in accordance with the present invention, a fluid supply system 43 is coupled to the collapsible sheath proximal end 33 of the collapsible sheath 22 in fluid communication with the tubular filament distal end 38.

In another embodiment in accordance with the present invention, the fluid expelled from the tubular filament distal end 38 is a solution provided to assist in the dislodgment, dissolution and/or breakup of the foreign matter. Fluids suitable for the particular purpose include, but are not limited to, anti-thrombolytic agents, Alkalol™, among others.

In another embodiment in accordance with the present invention, the fluid expelled from the tubular filament distal end 38 is a therapeutic agent added to provide integrity of the drainage system 2. Fluids suitable for the particular purpose include, but are not limited to, antibiotic agents and anti-neoplastic agents.

Once dislodged and/or broken up, the foreign material flows through the body tube lumen 15 to the canister tube 14 and drainage canister 16, as shown in FIG. 2.

In other embodiments in accordance with the present invention, the filament lumen 37 of the tubular filament 24b is adapted so as to permit the introduction of a sensor, such as, but not limited to, an ultrasound or other sensor device for diagnostic imaging within the body-space tube 10.

In other embodiments in accordance with the present invention, the filament lumen 37 of the tubular filament 24b is adapted to introduce cameras, or other devices into the body tube lumen 15 while maintaining a sterile environment with respect to body tube 10.

Figure 12A:
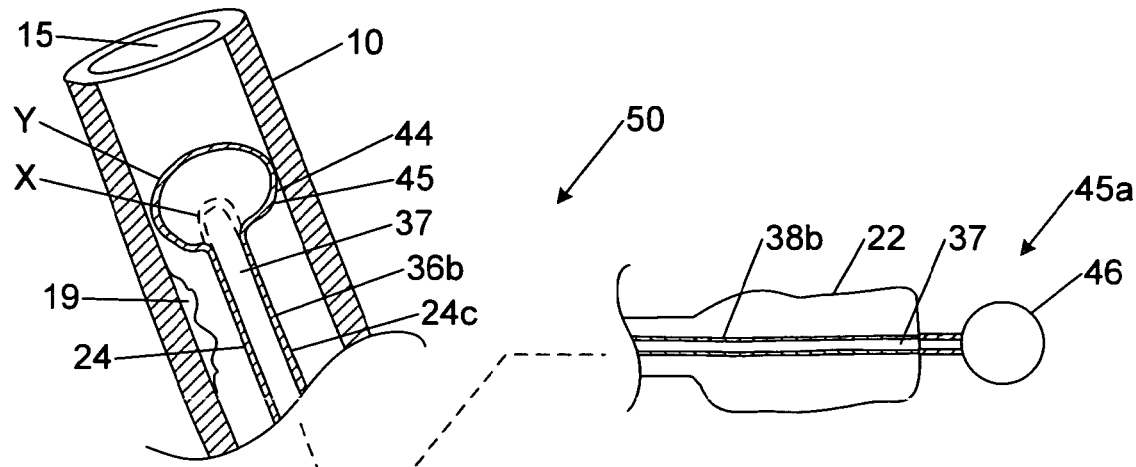
FIG. 12A is a partial side view of an expandable debris-removal system, wherein the cleaning member is a tubular filament comprising a tubular filament distal end having an expandable portion, in accordance with an embodiment of the present invention.

FIG. 12A is a partial side view of an expandable debris-removal system 50, wherein the cleaning member 24 is a tubular filament 24c comprising a tubular filament distal end 36b having an expandable portion 44 in fluid communication with a filament lumen 37, in accordance with an embodiment of the present invention. The expandable portion 44 is adapted to facilitate mechanical manipulation of the foreign material 19 to assist in the removal from the body tube lumen 15. The expandable portion 44 is adapted to have a relaxed state in which the tubular filament distal end 36 has a minimal profile X and an expanded state wherein the tubular filament distal end 36 has an enlarged profile Y. The expandable portion 44 is expanded by the advancement of inflation fluid from an inflation fluid delivery system 45, through the filament lumen 37 to the expandable portion 44. The inflation fluid is controlled at the tubular member proximal end 38b.

The expandable portion 44 is adapted to facilitate mechanical manipulation of the foreign material 19 to assist in the removal from the body tube lumen 15. The expandable portion 44 is advanced distal to (or beyond) the foreign material 19 while in a relaxed state. The expandable portion 44 is enlarged to take on a profile to at least partially occlude the body tube lumen 15. Withdrawal of the cleaning member 24 from the body tube lumen 15 causes the expanded portion 44 to abut and dislodge the foreign material 19, carrying the foreign material 19 distally to the canister tube 14.

In one embodiment in accordance with the present invention, the expandable portion 44 is adapted to fully occlude the body tube lumen 15, wherein the expandable portion 44 provides a squeegee action to clean the body tube lumen 15 of the foreign material 19.

In embodiments in accordance with the present invention, the fluid pressure of the inflation fluid is delivered to the expandable portion 44 by an external fluid source 45a comprising a reservoir 46 coupled to the filament lumen 37 at the tubular filament proximal end 38b of the cleaning member 24. In one embodiment in accordance with the present invention, a fluid pressure source 45a, such as, but not limited to, an elastic bulb or fluid-filled syringe, is provided exterior to the collapsible sheath 22 and coupled to the cleaning member 24 through a coupling. Sterility of the filament lumen 37 is not essential as the fluid is not in communication with the sterile drainage system 20.

Embodiments of the reservoir 46 comprise, among others, a compliant bulb, balloon, syringe, or other fluid supply means. In one embodiment wherein the reservoir is a compliant bulb, the bulb is compressed displacing the fluid from the reservoir 46 expanding the expandable portion 44. The compression of the bulb is subsequently relaxed to allow the fluid to return to the reservoir 46 and the expandable portion 44 to collapse to the original state.

Figure 12B:
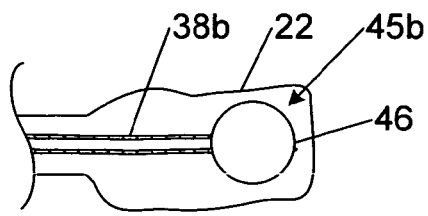
FIG. 12B is a partial side view of an expandable debris-removal system, wherein the cleaning member is a tubular filament comprising a tubular filament distal end having an expandable portion, in accordance with an embodiment of the present invention.

FIG. 12B illustrates yet another embodiment in accordance with the present invention, wherein the fluid source 45b, such as, but not limited to, an elastic bulb, is provided within the collapsible sheath 22. In this embodiment, the inflation fluid remains sterile in the event of rupture of the expandable portion 44.

In the embodiment of FIG. 12A, the expandable portion 44 is a bulb 45 at the tubular filament distal end 36b which is adapted to expand under fluid pressure and recoil back to substantially the original position upon withdrawal of the-fluid pressure. The tubular filament distal end 36b is adapted to expand in a substantially spherical confirmation. Such a configuration can be fabricated in a number of ways, including, but not limited to, preferential material thickness at the tubular filament distal end 36b such that the expandable portion 44 expands and the remaining portion of the tubular filament distal end 36b remains substantially unexpanded. In another embodiment, an expandable portion 44, such as a balloon, is coupled to the tubular filament distal end 36b.

Figure 13:
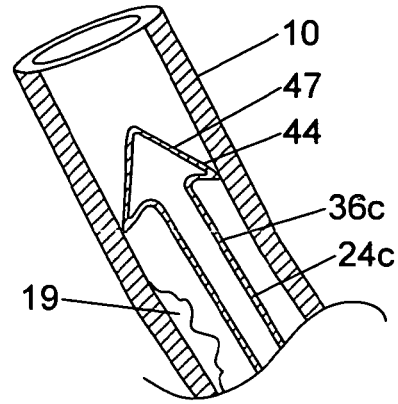
FIG. 13 is a side view of an arrowhead expandable distal tip having an arrowhead-shaped profile, in accordance with an embodiment of the present invention.

FIG. 13 is a side view of another embodiment of the tubular filament 24c in accordance with the present invention, comprising an expandable distal tip 47 having an arrowhead-shaped or umbrella profile. Such a configuration presents an aggressive structure for dislodging and/or breaking up foreign material 19 when pulled out of the body-space lumen 15. Other configurations are anticipated.

Figure 14:
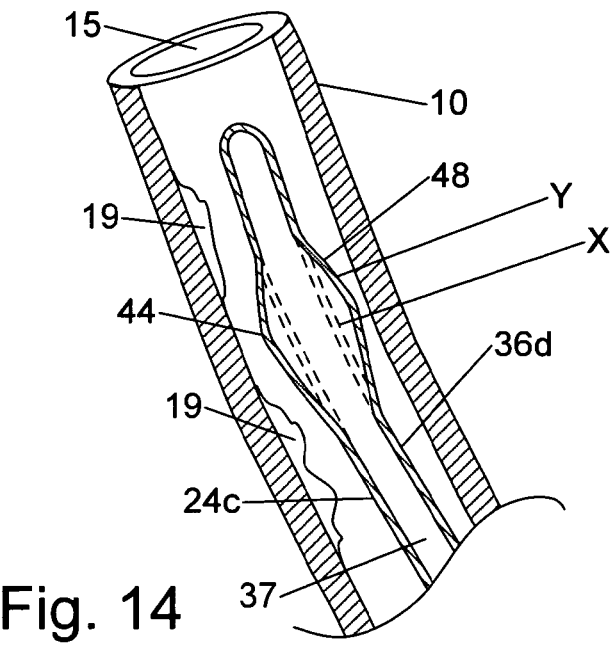
FIG. 14 is a side view of an expanding wall cleaning member comprising an expandable portion along a portion of the length of the distal end in accordance with an embodiment of the present invention.

FIG. 14 shows an embodiment of the present invention wherein the expanding portion 44 comprises an expanding wall portion 48 along a portion of the length of the tubular filament distal end 36b, in accordance with an embodiment of the present invention. The expandable wall portion 48 is in fluid communication with the filament lumen 37 and adapted so as to expand to an enlarged state Y from a relaxed state X upon presented with fluid pressure. The expandable wall portion 48 is adapted to expand or contract by the fluid therein. The fluid source is substantially the same as previously described and shown in FIGS. 12A and 12B, is adapted to pressurize the filament lumen 37 which in turn expands the expandable portion 44 to a larger diameter than the relaxed state. The tubular filament distal end 36d is advanced such that the expandable portion 44 extends beyond the foreign material 19 to be cleared from the body tube lumen 15. The fluid source is used to inflate the expandable wall portion 48 to a diameter sufficient so as to permit the advancement of the foreign material 19 down the body lumen 15 when the tubular filament 24c is pulled in a proximal direction.

In an embodiment in accordance with the present invention, as shown in FIGS. 12A, 13, and 14, the expandable portion 44 is integral with the tubular filament 24c.

Figure 15A:
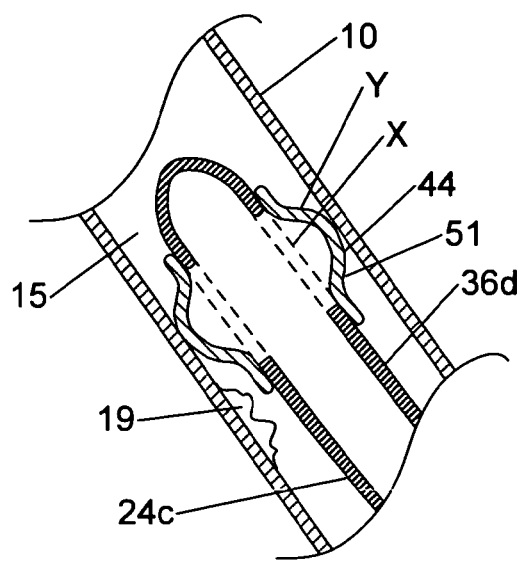
FIG. 15A is a side view of the distal end comprising an expandable portion not integral with the tubular filament, in accordance with an embodiment of the present invention.

FIG. 15A is a side view of the tubular filament distal end 36d comprising an expandable portion 44 not integral with, but coupled to, the tubular filament 24c, in accordance with an embodiment of the present invention. The expandable portion 44 is coupled to the tubular filament distal end 36d in manufacturing techniques employed, such as, but not limited to, in the production of angioplasty catheters. In one embodiment, the expandable portion 45 is a substantially non-resilient film material that is adapted to unfold and expand under internal fluid pressure and collapse and refold to a low profile upon the removal of internal fluid pressure.

In another embodiment, the expandable portion 44 comprises an elastic material adapted to substantially relax to the original state upon removal of the internal fluid pressure.

Figure 15B:
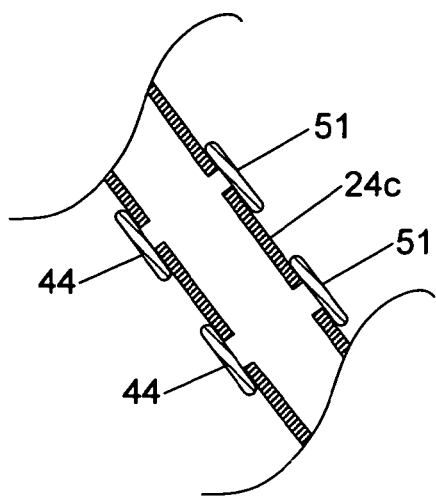
FIG. 15B is a side view of the distal end comprising a plurality of expandable portions not integral with the tubular filament, in accordance with an embodiment of the present invention.

FIG. 15B is a side view of the tubular filament distal end 36d comprising a plurality of expandable portions 44, in accordance with an embodiment of the present invention. The plurality of expandable portions 44 are spaced a predetermined distance apart along the length of the tubular filament 24c. Multiple expandable portions 44 provide additional cleaning surface for abutting, dislodging and moving of foreign material 19.

Figure 16A:
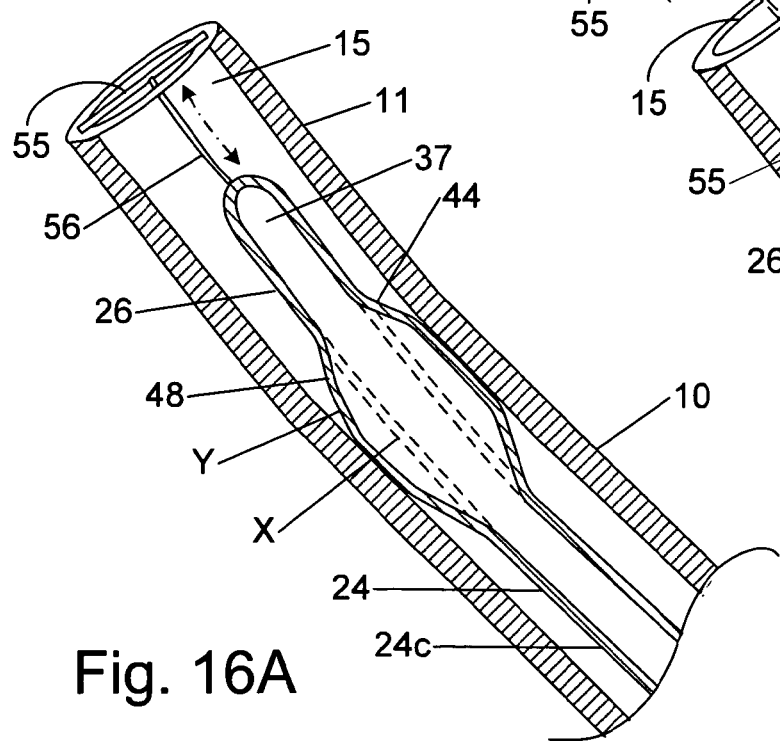
FIG. 16A is a side view of a distal end comprising an expandable portion, further comprising an elastic cord in accordance with an embodiment of the present invention.
Figure 16B:
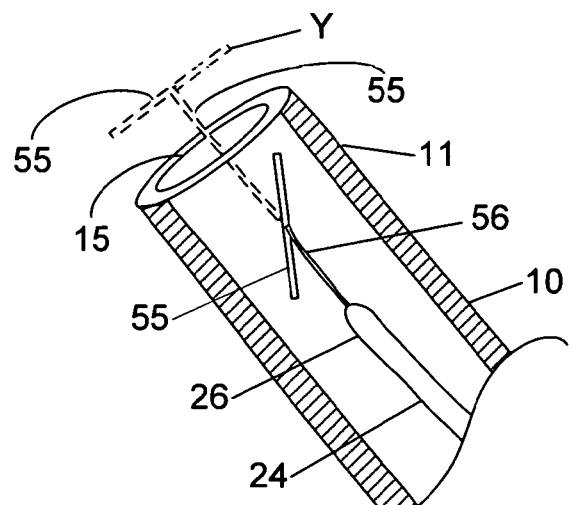
FIG. 16B is a side view of a distal end comprising an expandable portion, further comprising an elastic cord in accordance with an embodiment of the present invention.

FIG. 16A is a side view of a tubular filament distal end 36d comprising an expandable portion 44, further comprising an elastic cord 56, in accordance with an embodiment of the present invention. The elastic cord 56 is adapted to provide a restoring force to reposition the cleaning member 24 adjacent the body tube distal end 11. The elastic cord 56 is coupled to the body tube distal end 11 and the cleaning member distal end 26. As the cleaning member 24 is withdrawn from the body tube 10, the elastic cord 56 presents a return force to bring the cleaning member distal end 26 back to the body tube distal end 11.

The elastic cord 56 comprises an elastic property and undergoes tension as the cleaning member 24 is retracted into the collapsible sheath 22, and, upon release of the cleaning member proximal end 28 of the cleaning member 24, the cleaning member distal end 26 is drawn towards the body tube distal end 11.

In the embodiment in accordance with FIG. 16A, the cleaning member 24 further comprises a cross-bar support 55 adapted to couple the cleaning member 24 to the body tube distal end 11. The cleaning member 24 is advanced to adjacent the body tube distal end 11, wherein the cross-bar support 55 is slidingly received in the body tube lumen 15 at an acute angle with the axis of the body tube lumen 15. The cleaning member 24 is advanced such that the cross-bar support 55 exits the body tube lumen 15. The cross-bar support 55 turns substantially perpendicular to the body tube 10 and acts as an anchor for the elastic cord 56 at the body tube distal end 11.

FIG. 17 is a side view of a distal end of an umbrella cleaning member 60 comprising an umbrella-lice expandable portion 58 comprising of a plurality of struts 57 and webs 59, in accordance with an embodiment of the present invention. The cleaning member 24 comprises a flexible filament having an umbrella-like expandable portion 58 coupled to the filament distal end 36e. The umbrella cleaning member 60 is adapted to collapse to a narrow profile X when advancing beyond the foreign material 19, and expand to substantially occlude the body tube lumen 15 when withdrawn, abutting and pushing the foreign material 19 towards the body tube proximal end 13.

FIG. 18 is a side view of a distal end of a cleaning member comprising an umbrella-like expandable portion 58 comprising of a plurality of struts 57 and webs 59 lifting and moving the foreign material 19 distally from the body tube lumen 15. In the expanded state, the webs 59, carried by the struts 57, open to at least substantially occlude the body tube lumen 15 and form an apex 61 pointing distally. The struts 57 and the webs 59 provide a structure that is adapted to breakup and/or remove foreign material 19 from the body tube lumen 15 as the cleaning member 24 is advanced proximally.

In another embodiment in accordance with the present invention, referring again to the embodiment of FIG. 17, the umbrella cleaning member 60 is coupled to the body tube distal end 11 with a cord 56 substantially as described above.

FIG. 19 is a side view of a distal end of a cleaning member 24 comprising an umbrella-like expandable portion 58 comprising of a plurality of struts 57 and webs 59 returning (moving distally) to the body tube distal end 11. The struts 57 and webs 59 fold down to a low profile X and substantially parallel with the body tube lumen 15 when returning to the body tube distal end 11 and when the cord 56 is in the relaxed state. The undeployed position allows the cleaning member 24 to transit past any remaining foreign material 19 that was not removed subsequently, as well as allow the continuous flow of drainage fluid.

The umbrella-like expandable portion 58 is adapted to mechanically clean the body tube lumen 15 by mechanical dislodgment of the foreign material 19. The cleaning member 24c is sufficiently flexible to traverse the curvature of the body tube lumen 15, but is sufficiently rigid so as to not buckle when advanced through the body tube lumen 15 by pushing from the proximal end and to advance past the foreign material 19. Further, the umbrella-lice expandable portion 58 is sufficiently stiff when expanded so as to dislodge the foreign material 19 within the body tube lumen 15 as it makes contact therewith.

FIG. 20 is a side view of a cleaning member distal end 36e of a cleaning member 24 comprises a plurality of umbrella-like expandable portions 58 comprising of a plurality of struts 57 and webs 59, in accordance with an embodiment of the present invention. The plurality of umbrella-like expandable portions 58 are coupled to either adjacent umbrella-like expandable portions 58 or to the body tube distal end 11 with an elastic cord 56. Having more than one umbrella-like expandable portion 58 reduces the extent in which each umbrella-like expandable portion 58 needs to traverse within the body tube lumen 15. In addition, each cord 56 may elongate independently from each other. It is anticipated that if the umbrella-like expandable portions 58 exhibit significant friction against the body tube lumen 15, multiple elastic cords 56 my stretch disproportionate to other elastic cords 56 in a multiple elastic cord system.

The umbrella-like expandable portions 58 are adapted to present a folded/compressed/closed state and an unfolded/extended/open state. The umbrella-like expandable portions 58 adapted to open when the cleaning member proximal end 38 is pulled causing the umbrella-like expandable portions 58 to advance towards the body tube proximal end 13, and to close when the cleaning member proximal end 38 is released causing the umbrella-like expandable portions 58 to be drawn towards the body tube distal end 11.

Figure 21:
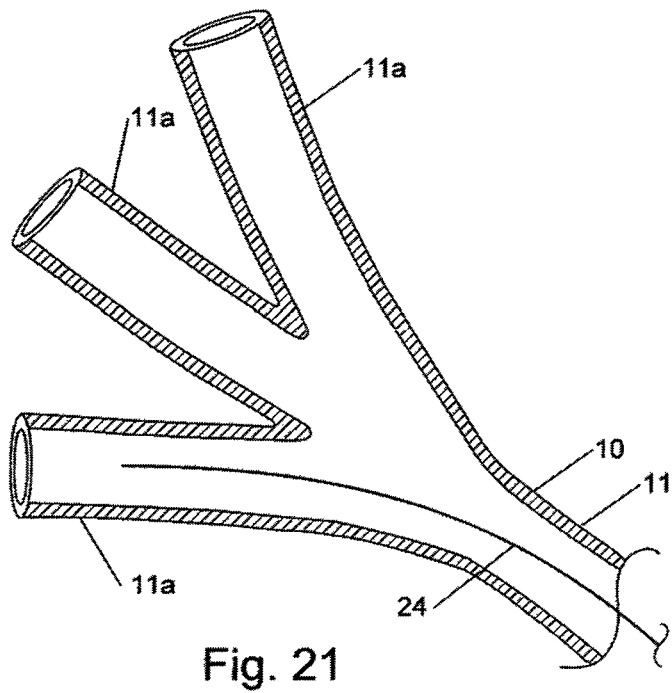
FIG. 21 is a side view of a distal end of a body tube that is bifurcated into a plurality of body tube distal ends in accordance with an embodiment of the present invention.
Figure 22:
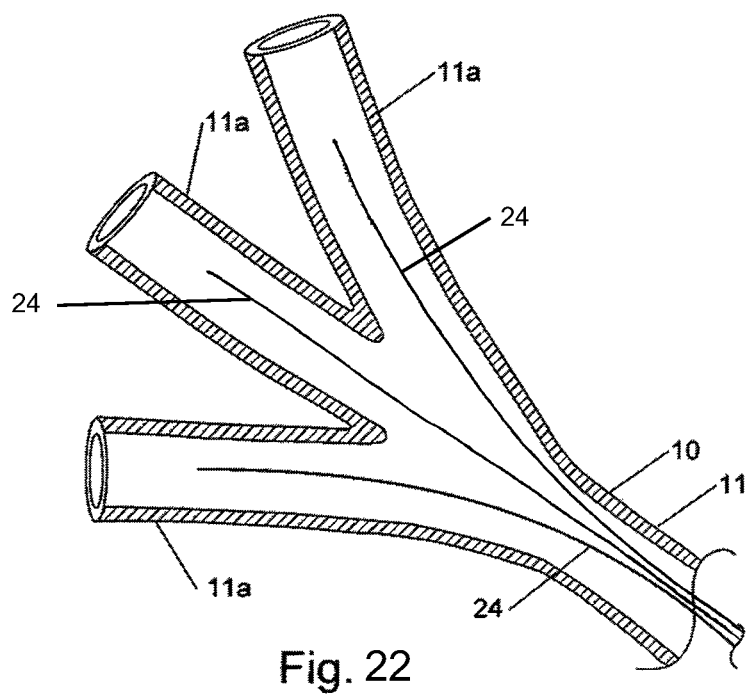
FIG. 22 is a side view of a distal end of a body tube that is bifurcated into a plurality of body tube distal ends, wherein each body tube distal end is associated with a cleaning member, in accordance with an embodiment of the present invention.

FIG. 21 is a side view of a distal end 11 of a body tube that bifurcates into a plurality of body tube distal ends 11a, in accordance with an embodiment of the present invention. The body tube cleaning member 24 of the debris-removal system is adapted to be able to traverse any one of the multiple body tube distal ends 11a.

In another embodiment of the present invention, a plurality of body-space drainage tubes are received within the body that are interconnected internal to the body forming a single drainage tube exiting out of one puncture site, such as, but not limited to, bifurcated or trifurcated tube, permitting the tubes to be kept clear from one proximal location, the cleaning member having a plurality of distal cleaning members corresponding to the plurality of drainage tubes.

Other embodiments of the present invention include a small diameter body tube that enters the patient's chest via a small hole. Once inside the chest, the tube divides into two or more ends, herein called phalanges. Within each phalange is a tube clearing device, as described above. In one application, by way of example, one phalange is positioned over the surface of the heart, one is positioned along the inferior surface of the heart, and one is positioned in the left chest. AU drain to a single tube that exits the body. In this embodiment, all the critical areas of the chest are drained through a single tube that exits the chest wall and skin.

Likewise, after lung or pleural surgery, one phalange is positioned along the medial surface of the lung, one along the base along the diaphragm, and one along the posterior gutter going to the apex. In this way, all the critical areas of the chest are drained after lung surgery with a single tube exiting the skin and chest wall. Efficacy is maintained, or even increased, and invasiveness, pain, and ultimately cosmesis, are all positively addressed. Multiple double-lumen tubes are bonded together using thin, polymeric severable membranes with a single common connector being attached to one end of the tubes.

After the multi-lumen tubes are inserted into the chest cavity through a single entry in the chest wall, they can be severed to form individual multi-lumen tubes which can be positioned to drain various sites inside the chest cavity. The reduction of insertion sites lessens the possibility of potential chest-tube-site infections. Various embodiments of the present invention provide a cleaning member that advances in and out of the body tube lumen. Embodiments of the present invention provides that body tubes can be miniaturized Clinicians can choose smaller diameter/lumen body tubes or catheters for drainage if the fear of clotting and clogging is reduced or eliminated. For example, if, for fear of clogging, one routinely uses a 36 F catheter after heart surgery, with embodiments of the present invention, one could use an 8 or 10 F tube, which would hurt less while in place, hurt less when removed, and leave a smaller scar. Furthermore, since smaller tubes could be more readily used, they could be more readily inserted by a wider base of practitioners, due to the reduced need for expertise to insert and clinically manage the tube. Smaller holes mean less pain, less risk of infection, and less risk that the patient will have a complication from air sucking back into the chest through the hole left in the chest wall while it is healing. Larger holes require a stitch to close, and stitches need to be removed, which is time-consuming for the clinician and painful and inconvenient for the patient. A 10 F hole could be easily closed with a bandage, rather than requiring a stitch.

What is claimed is:

1. A method of clearing debris from a body tube, comprising:
   a. drawing suction through a proximal end of a body tube whose distal end is implanted in a patient's body cavity, wherein the body tube partially defines a closed-suction system;
   b. draining a fluid from the patient's body cavity through the proximal end of the body tube; and
   c. actuating from outside the body tube a cleaning member within a lumen of the body tube to dislodge debris therein, without interrupting the suction within the closed-suction system, wherein the cleaning member comprises a flexible wire filament that extends distally from a proximal opening of the body tube.

2. The method of claim 1, wherein said actuating the cleaning member does not compromise a sterile field within the body tube.

3. The method of claim 1, the cleaning member comprising a distal end and a cleaning head disposed at or adjacent the distal end of the flexible wire filament.

4. The method of claim 3, the cleaning head being configured such that it permits free flow of material past the cleaning head through the lumen of the body tube regardless whether the cleaning head is at rest or is being actuated to dislodge debris.

5. The method of claim 3, the cleaning member being configured such that the distal end cannot exit the body tube distal end upon advancement of the cleaning member.

6. The method of claim 3, wherein actuating the cleaning member causes a corresponding actuation of the cleaning head against an interior wall surface of the lumen of the body tube.

7. The method of claim 3, further comprising expelling a fluid from the distal end.

8. The method of claim 3, further comprising a filament manipulation device coupled to a proximal end of the cleaning member.

9. The method of claim 8, wherein the filament manipulation device is configured to impart vibratory excitation to the cleaning member.

10. The method of claim 1, wherein debris dislodged by the cleaning member is drawn through the lumen of the body tube and out the proximal end thereof.

11. The method of claim 1, further comprising inserting the cleaning member through a collapsible sheath in communication with the body tube.

* * * * *